United States Patent [19]

Schnoor

[11] Patent Number: 4,832,017

[45] Date of Patent: May 23, 1989

[54] BREATHING MASK

[75] Inventor: Christian Schnoor, Lübeck, Fed. Rep. of Germany

[73] Assignee: Drägerwerk Aktiengesellschaft, Lübeck, Fed. Rep. of Germany

[21] Appl. No.: 31,943

[22] Filed: Mar. 27, 1987

[30] Foreign Application Priority Data

Mar. 27, 1986 [DE] Fed. Rep. of Germany ....... 3610493

[51] Int. Cl.⁴ ................................................. A62B 7/10
[52] U.S. Cl. .......................... 128/206.12; 128/206.21; 128/206.28
[58] Field of Search ....................... 128/201.23, 203.29, 128/205.25, 206.12, 206.16, 206.17, 206.21, 206.24, 206.28

[56] References Cited

U.S. PATENT DOCUMENTS

| | | | |
|---|---|---|---|
| 1,127,612 | 2/1915 | Furtaw | 128/206.28 |
| 1,142,990 | 6/1915 | Stern | 128/206.16 |
| 2,070,754 | 2/1937 | Schwartz | 128/206.12 |
| 2,281,181 | 4/1942 | Clarke | 128/201.23 |
| 4,126,131 | 11/1978 | Davis et al. | 128/205.25 |
| 4,337,767 | 7/1982 | Yahata | 128/206.26 |
| 4,454,881 | 6/1984 | Huber et al. | 128/206.16 |
| 4,573,463 | 3/1986 | Hall | 128/206.28 |

FOREIGN PATENT DOCUMENTS 2059782 4/1981 United Kingdom ........... 128/206.12

OTHER PUBLICATIONS

Hubner-Gummi Und Kunststoff-GmbH, "Strahlen Ver-Netzte Formteile Aus PVC".
Rompps Chemie-Lexikon.
Tetzlaff, "Thermisch Vernetztes Polysulfon", 1986.

Primary Examiner—Edward M. Coven
Assistant Examiner—John P. Lacyk
Attorney, Agent, or Firm—Walter Ottesen

[57] ABSTRACT

A breathing mask has an elastic molded body which has area zones of materials of different hardnesses. This breathing mask is improved such that even with a one-piece molded configuration of the breathing mask, area zones of different hardness and constant wall thickness are provided. For this purpose, area zones integrated into the molded body are reinforced differently by means of a partial heat treatment.

4 Claims, 1 Drawing Sheet

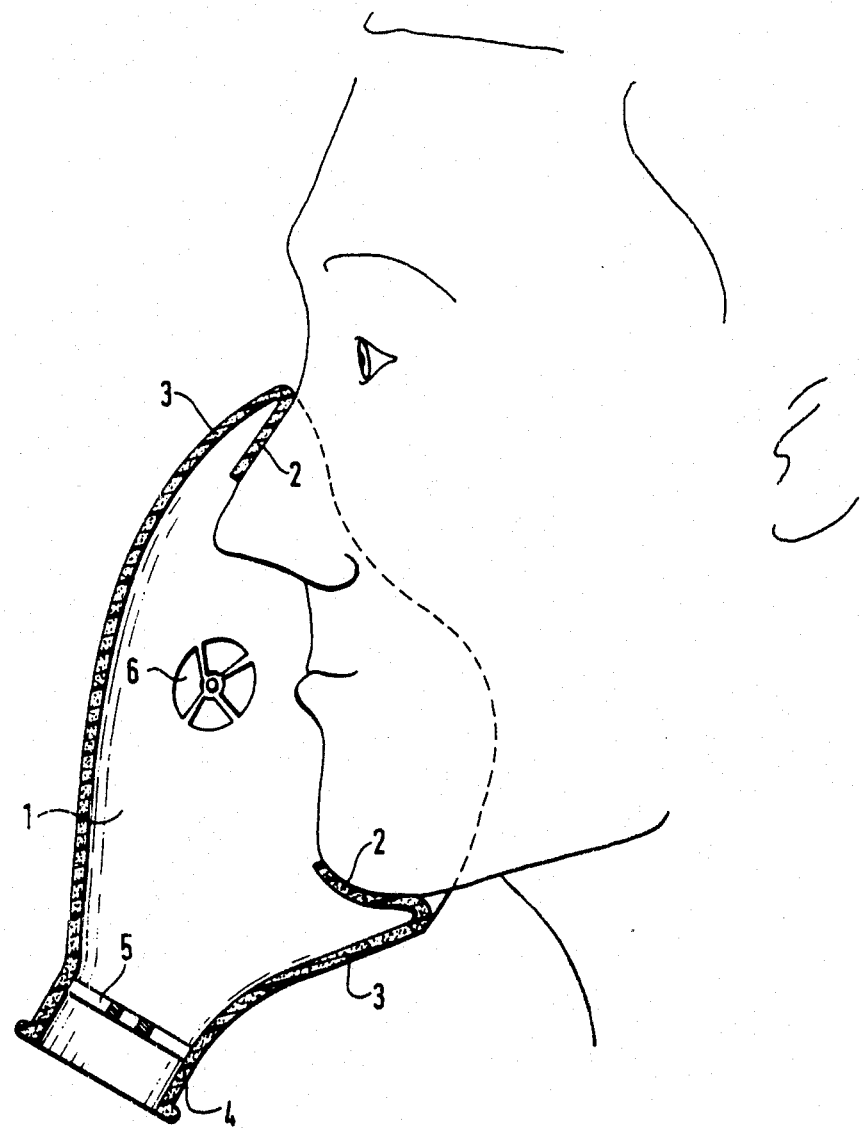

BREATHING MASK

FIELD OF THE INVENTION

The invention relates to a breathing mask made of an elastic molded body which has zones of materials having various hardness.

BACKGROUND OF THE INVENTION

A breathing mask of this kind is known from German Utility Model Application No. 67 52 895.

The known breathing mask has a molded body which can be placed over the area of the nose and mouth. The ambient air can be inhaled through a filter and is exhaled again through an exhalation valve. A bead of expandable plastic is provided for reliably sealing off the breathing mask at the surface of the skin in the nose and mouth area of the wearer. This peripheral bead is formed when the mask body is molded by appropriately increasing the cross section of the mold. Other regions of the mask body are provided with reinforcing elements such as metal sheets or plastic inlays which are inlaid into the appropriate molding tool during molding. The known breathing masks thus have a bead seated on and surrounding parts of the face of the wearer. The bead is made of soft plastic and the mask has a reinforced mask body for receiving a breathing filter or for mounting the exhalation valve.

In the known breathing masks, the soft configuration of various parts of the mask is attained only by a corresponding thickening of the cross section, so that there the expandable plastic can form a porous elastic core. A variable distribution of hardness in the mask body is therefore always associated with a variable wall thickness distributed over the mask. Freedom of design for the purpose of attaining a breathing mask that is comfortable to wear is considerably restricted thereby. Furthermore, the weight of the breathing mask is increased because of the inlaid reinforcing elements.

In other breathing masks, which are not made of expandable plastics, different wall thicknesses of relatively soft plastics are used. The masks are then made thin in the parts around the face. Locations that should be stronger are attained by means of larger wall thicknesses to very large wall thicknesses. These breathing masks have a high inherent weight because of the accumulation of larger wall thicknesses in the middle region of the mask.

SUMMARY OF THE INVENTION

It is accordingly an object of the invention to provide a breathing mask that has area zones of different hardnesses and constant wall thickness notwithstanding that the mask is molded as a single piece.

According to a feature of the invention, the area zones integrated into the molded body are reinforced differently by means of a partial hardening treatment.

The most important advantage of the invention is that by using fewer inlayed parts and providing fewer accumulations of material, the breathing mask is lighter in weight. Furthermore, a breathing mask having a varying distribution of hardness in the mask body still has a constant wall thickness.

In a particularly simple manner and for reinforcing the area zones, the corresponding portions of the breathing mask can be hardened by irradiating the same with X-rays. Accordingly, and in a directed manner and without restricting the desired molding, individual regions of the breathing mask made of PVC plastic can be configured with different hardnesses. Processes of hardening plastics per se by irradiating the same with X-rays are known commercial practices, for example, by the Raychem Corporation, a corporation organized and doing business in the United States of America.

It is also advantageous for molding purposes to add different proportions of hardeners or softeners to the plastic at the area zones, or to remove different proportions of hardeners or softeners therefrom.

A partial hardening treatment can also be performed in a suitable manner in that during molding, the different area zones are molded together from materials of different hardnesses. For example, PVC plastic and rubber material can be molded together in predetermined amounts to achieve different degrees of hardness.

BRIEF DESCRIPTION OF THE DRAWING

The invention will now be described with reference to the single drawing FIGURE which is a schematic view of an embodiment of a breathing mask according to the invention.

DESCRIPTION OF THE PREFERRED EMBODIMENTS OF THE INVENTION

The breathing mask shown in the drawing has a molded body 1 which rests with a sealing edge 2 on the face of a wearer. The cylindrical connection 4 serves to receive a flexible tube. A receiving means is located in the hose connection 4 for the inhalation valve 5. The recess for an exhalation valve 6 is attached to the mask wall.

The breathing mask shown is configured as one piece, and the individual area zones have different material hardnesses because of partial heat treatment. For instance, the molded body 1, as a hard area zone, is hardened further once molding is completed in order to obtain a stable shape. In contrast, the sealing edge 2, as an area zone having very slight hardness, remains untreated to enable a gentle contact of the breathing mask with face of the wearer. In the transitional zone 3 around the sealing edge 2, the plastic changes from the soft range to the hard range. The regions for the inhalation valve 5, exhalation valve 6 and hose connection 4 are configured so as to be hard.

It is understood that the foregoing description is that of the preferred embodiments of the invention and that various changes and modifications may be made thereto without departing from the spirit and scope of the invention as defined in the appended claims.

What is claimed is:
1. A breathing mask comprising:
   an elastic preformed body made of only a single piece of mask material;
   said elastic body having a first region for contact engaging the face of the wearer, said first region having a predetermined first degree of stiffness;
   said elastic body having a second region adjacent said first region;
   said second region having a second degree of stiffness greater than the stiffness of said first region, said second degree of stiffness being imparted to said second region by a partial hardening treatment utilizing energetic radiation; and,
   said regions of said body having substantially the same wall thickness irrespective of said degrees of stiffness.

2. The breathing mask of claim 1, said elastic formed body being made of plastic.

3. A breathing mask comprising:

an elastic preformed body made of only a single piece of mask material;

said elastic body having a first region for contact engaging the face of the wearer, said first region having a predetermined first degree of stiffness;

said elastic body having a second region adjacent said first region;

said second region having a second degree of stiffness different than the stiffness of said first region; and, one of said degrees of stiffness being imparted to the region corresponding thereto by a partial hardening treatment utilizing energetic radiation.

4. The breathing mask of claim 3, said portions of said body having substantially the same wall thickness irrespective of said degrees of stiffness.

* * * * *